United States Patent
Ye

(10) Patent No.: US 9,126,928 B2
(45) Date of Patent: Sep. 8, 2015

(54) 4-HYDROXY-2-OXO-1-PYRROLIDINE ACETAMIDE RACEMATE CRYSTAL FORM I AND PREPARATION METHOD THEREFOR

(75) Inventor: Lei Ye, Chongqing (CN)

(73) Assignee: Chongqing Runze Pharmaceutical Co., Ltd., Chongqing (CN)

( * ) Notice: Subject to any disclaimer, the term of this patent is extended or adjusted under 35 U.S.C. 154(b) by 0 days.

(21) Appl. No.: 14/237,893

(22) PCT Filed: Apr. 24, 2012

(86) PCT No.: PCT/CN2012/074573
§ 371 (c)(1),
(2), (4) Date: Apr. 10, 2014

(87) PCT Pub. No.: WO2013/020390
PCT Pub. Date: Feb. 14, 2013

(65) Prior Publication Data
US 2014/0221670 A1    Aug. 7, 2014

(30) Foreign Application Priority Data
Aug. 11, 2011  (CN) .......................... 2011 1 0230079

(51) Int. Cl.
*C07D 207/273*    (2006.01)

(52) U.S. Cl.
CPC ................................. *C07D 207/273* (2013.01)

(58) Field of Classification Search
None
See application file for complete search history.

(56) References Cited

FOREIGN PATENT DOCUMENTS

CN    102101836 A  *  6/2011

OTHER PUBLICATIONS

Machine translation of CN102101836A (Jun. 22, 2011).*

* cited by examiner

*Primary Examiner* — Michael Barker
(74) *Attorney, Agent, or Firm* — Leong C. Lei

(57) ABSTRACT

Disclosed is a 4-hydroxy-2-oxo-1-pyrrolidineacetamide racemate crystal form I which is prepared by the following steps: dissolving crude 4-hydroxy-2-oxo-1-pyrrolidineacetamide racemate in a solvent such as a micromolecular alcohol to form a saturated solution; heating and stirring the solution overnight at 38~42° C. to obtain a suspended precipitate; filtering and drying the solution to obtain a crystal. Such 4-hydroxy-2-oxo-1-pyrrolidineacetamide racemate crystal form I has a purity as high as 99.5%, which has significant treatment effect on curing respective diseases, and the 4-hydroxy-2-oxo-1-pyrrolidineacetamide racemate crystal form I has the features of simple manufacturing method, mild control condition, and low production cost, and its yield rate is as high as 99.5% which is applicable for mass production.

10 Claims, 3 Drawing Sheets

4-HYDROXY-2-OXO-1-PYRROLIDINE ACETAMIDE RACEMATE CRYSTAL FORM I AND PREPARATION METHOD THEREFOR

FIELD OF THE INVENTION

The present invention relates to a 4-hydroxy-2-oxo-1-pyrrolidineacetamide drug, in particular to a 4-hydroxy-2-oxo-1-pyrrolidineacetamide racemate crystal form I and its preparation method.

BACKGROUND OF THE INVENTION 4-hydroxy-2-oxo-1-pyrrolidineacetamide is a new-generation brain metabolism improving drug, and pyrrolidinones (GABOB) derivatives and piracetam-like drugs are capable of promoting the synthesis of phosphorylcholine and phosphoryl ethanolamine to promote brain metabolism, and providing a stimulating effect to specific central nervous pathway through blood brain barrier to improve intelligence and memory. The 4-hydroxy-2-oxo-1-pyrrolidineacetamide has a good medical treatment effect on cerebrovacular disease, brain injury, brain tumor (after surgery), and intracranial infection, dementia, and cerebral degenerative disorder. The drug is applicable for memory and intelligence disorders caused by mild to moderate vascular dementia, senile dementia and brain trauma. The 4-hydroxy-2-oxo-1-pyrrolidineacetamide was first synthesized by Smithkline Beecham (Italia) in 1974 and launched in 1987, and this drug can promote the synthesis of phosphorylcholine and phosphoryl ethanolamine to promote brain metabolism, and is particularly effective to memory and concentration and has a better effect than piracetam, and the toxicity of the drug is low. The 4-hydroxy-2-oxo-1-pyrrolidineacetamide is a racemate composed of two isomers, respectively: (S)-4-hydroxy-2-oxo-1-pyrrolidineacetamide and (R)-4-hydroxy-2-oxo-1-pyrrolidineacetamide, and it has a chemical name of 4-hydroxy-2-oxo-1-pyrrolidineacetamide and a chemical structure as follows:

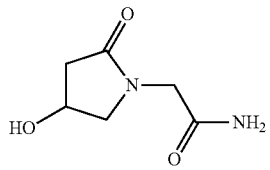 [SMILES: NC(=O)CN1CC(O)CC1=O]

The method for synthesizing 4-hydroxy-2-oxo-1-pyrrolidineacetamide, the method for preparing an injection agent and a dispersible tablets of the 4-hydroxy-2-oxo-1-pyrrolidineacetamide and the products thereof have been disclosed in journals and literatures, but there is still no report on the subject related to the 4-hydroxy-2-oxo-1-pyrrolidineacetamide racemate form yet.

SUMMARY OF THE INVENTION

In view of the aforementioned shortcomings of the prior art, it is a primary objective of the present invention to overcome the shortcomings by providing a 4-hydroxy-2-oxo-1-pyrrolidineacetamide racemate crystal form I with a high purity and a good medical treatment effect.

At present, no 4-hydroxy-2-oxo-1-pyrrolidineacetamide racemate crystal form related report is found, and the inventor of the present invention names the 4-hydroxy-2-oxo-1-pyrrolidineacetamide racemate crystal form as 4-hydroxy-2-oxo-1-pyrrolidineacetamide racemate crystal form I.

Another objective of the present invention is to provide a method for preparing the above-mentioned 4-hydroxy-2-oxo-1-pyrrolidineacetamide racemate crystal form I, and the prepared 4-hydroxy-2-oxo-1-pyrrolidineacetamide racemate crystal form I has low impurity (or high purity).

To achieve the aforementioned objectives, the present invention provides a 4-hydroxy-2-oxo-1-pyrrolidineacetamide racemate crystal form I having a diffraction peak at a diffraction angle 2θ such as 12.011, 15.318, 17.407, 19.633, 21.228, 22.052, 24.577, 25.223, 27.647, 28.161, 29.109, 30.805, 31.276, 31.766, 32.77, 33.477, 35.252, 35.645, 36.236, 37.379, 39.56, 40.489, 41.256, 41.948, 43.443 or 44.628 degrees.

The 4-hydroxy-2-oxo-1-pyrrolidineacetamide racemate crystal form I has X-ray diffraction powder data expressed by the following d (Å) values and relative intensity percentage I values (%),

| d value | I value | d value | I value |
|---|---|---|---|
| 7.3623 | 3.6 | 5.7794 | 11.6 |
| 5.0905 | 34.7 | 4.5179 | 51.2 |
| 4.1820 | 100.0 | 4.0275 | 5.8 |
| 3.6192 | 49.1 | 3.5278 | 6.4 |
| 3.2238 | 15.6 | 3.1661 | 13.2 |
| 3.0652 | 10.4 | 2.9002 | 1.3 |
| 2.8576 | 1.4 | 2.8146 | 5.6 |
| 2.7306 | 12.3 | 2.6746 | 5.6 |
| 2.5438 | 5.0 | 2.5167 | 8.4 |
| 2.4770 | 7.9 | 2.4038 | 1.9 |
| 2.2762 | 2.3 | 2.2261 | 3.7 |
| 2.1865 | 1.5 | 2.1520 | 2.6 |
| 2.0813 | 1.8 | 2.0287 | 1.3 |

The 4-hydroxy-2-oxo-1-pyrrolidineacetamide racemate crystal form I has a X-ray diffraction powder chart as shown in FIG. 1.

The 4-hydroxy-2-oxo-1-pyrrolidineacetamide racemate crystal form I has an absorption peak in an infrared spectrum produced by the 4-hydroxy-2-oxo-1-pyrrolidineacetamide racemate crystal form I in a wave number such as 3426 ($cm^{-1}$), 3330 ($cm^{-1}$), 3276 ($cm^{-1}$), 3235 ($cm^{-1}$), 2931 ($cm^{-1}$), 2876 ($cm^{-1}$), 1665 ($cm^{-1}$), 1593 ($cm^{-1}$), 1480 ($cm^{-1}$), 1452 ($cm^{-1}$), 1428 ($cm^{-1}$), 1320 ($cm^{-1}$), 1272 ($cm^{-1}$), 1220 ($cm^{-1}$), 1078 ($cm^{-1}$), 974 ($cm^{-1}$), 941 ($cm^{-1}$), 757 ($cm^{-1}$), 702 ($cm^{-1}$), 602 ($cm^{-1}$), 517 ($cm^{-1}$), or 450 ($cm^{-1}$).

The method of preparing the aforementioned 4-hydroxy-2-oxo-1-pyrrolidineacetamide racemate crystal form I comprises the following steps:
(1) Dissolve a crude 4-hydroxy-2-oxo-1-pyrrolidineacetamide racemate in a micromolecular alcohol to obtain a saturated solution.
(2) Heat the saturated solution and stir the saturated solution overnight at 38~42° C. to obtain a suspended precipitate.
(3) Filter and dry the suspended precipitate to obtain a crystal.

To further improve the purity and yield rate of the 4-hydroxy-2-oxo-1-pyrrolidineacetamide racemate, the micromolecular alcohol is preferably isopropanol, and the stirring temperature is approximately 40° C., and the stirring time is approximately 7 hours.

More specifically, the method for preparing the 4-hydroxy-2-oxo-1-pyrrolidineacetamide racemate crystal form I comprises the following steps:

(1) Dissolve a crude 4-hydroxy-2-oxo-1-pyrrolidineacetamide racemate in isopropanol to obtain a saturated solution, and precipitate the solution to obtain a suspended substance.
(2) Heat the suspended substance at 40° C. and stir it for 7 hours to obtain a suspended precipitate.
(3) Filter and dry the suspended precipitate in vacuum for 24 hours to obtain a powdered crystal.

The present invention has the following effects:

The 4-hydroxy-2-oxo-1-pyrrolidineacetamide racemate crystal form I of has a purity as high as 99.5%, which has significant treatment effect on curing respective diseases, and the 4-hydroxy-2-oxo-1-pyrrolidineacetamide racemate crystal form I has the features of simple manufacturing method, mild control condition, and low production cost, and its yield rate is as high as 99.5% which is applicable for mass production.

DESCRIPTION OF THE PREFERRED EMBODIMENTS

Figure 1:
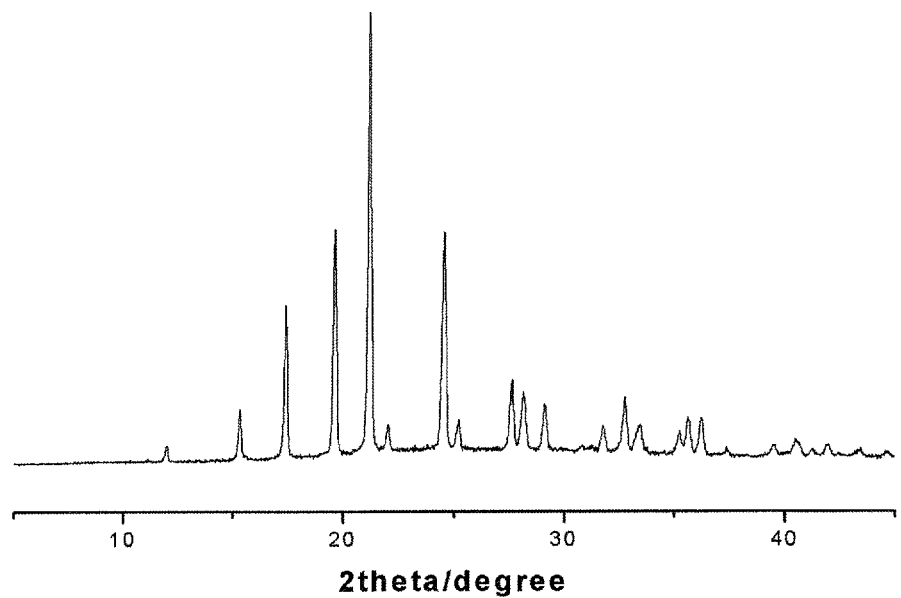
FIG. 1 is a powder diffraction chart of a 4-hydroxy-2-oxo-1-pyrrolidineacetamide racemate crystal form I of the present invention.

The aforementioned and other objectives and advantages of the present invention will become clearer in light of the following detailed description of an illustrative embodiment of this invention described in connection with the drawings. It is intended that the embodiments and drawings disclosed herein are to be considered illustrative rather than restrictive.

Preferred Embodiment 1

Dissolve 50 mg of a crude 4-hydroxy-2-oxo-1-pyrrolidineacetamide racemate in an anhydrous methanol, stir the solution overnight, filer the solution, allow the solution to stand still in a dryer, and evaporate the solvent to obtain a colorless transparent crystal with a yield rate of 82% and a purity of 99.4%.

The crude 4-hydroxy-2-oxo-1-pyrrolidineacetamide racemate of the present invention is synthesized according to the following steps, and its purity is 98.5%:

(a) Add 139.6 g of glycine ethyl ester hydrochloride into 1100 ml of anhydrous ether, ice cold the solution to −6° C. by passing 27.2 g of ammonia gas, so that the glycine ethyl ester hydrochloride is ionized to form glycinate, wherein the proportion of glycine ethyl ester hydrochloride:anhydrous ether:ammonia gas is 1 mol: 1100 ml:1.6 mol.

(b) Add 336 ml of anhydrous ethanol and 67.2 g of sodium bicarbonate into the aforementioned product, and drop 166.6 g of 4-chloro-3-hydroxy-butyrate into the solution, wherein the dropping time is 1.8 hours, and the reaction takes place at 72° C. for 22 hours under the condition of pH value=8.

(c) Filter the solution and rinse the filtered solution thoroughly by ethanol, concentrate the solution, dissolve the concentrated substance in water, add butyrate (of a weight equal to 7 times of the weight of the filtered solution) for extraction, concentrate the water phase, separate the perform a column chromatography, and finally add aqueous ammonia with a concentration of 23%. The reaction takes place at 22° C. for 4 fours to obtain a crude oxiracetam, wherein the consumption of 23% aqueous ammonia is equal to 13 times of the product of the column chromatography.

Wherein, the proportion of glycinate:sodium bicarbonate:4-chloro-3-hydroxy-butyrate=1:0.8:1 calculated by molar ratio, and the consumption of anhydrous ethanol is equal to 5 times of the weight of sodium bicarbonate.

(d) The crude is prepared by dissolving the aforementioned product in water, and 732# strong acid cation exchange resin and the 711 # strong alkali cation exchange resin are passed into the solution, and the collected solution is concentrated, wherein the ratio of the crude:water=1 g:0.5 ml, and the ratio of the crude product:the strong acid cation exchange resin=1 g:10 ml.

Preferred Embodiment 2

Dissolve 100 mg of a crude 4-hydroxy-2-oxo-1-pyrrolidineacetamide racemate in ethanol (95%), stir the solution overnight, filer the solution, allow the solution to stand still in a dryer, and evaporate the solvent to obtain a colorless transparent crystal with a yield rate of 85% and a purity of 99.2%.

Preferred Embodiment 3

Dissolve 50 mg of a crude 4-hydroxy-2-oxo-1-pyrrolidineacetamide racemate in isopropanol, stir the solution overnight, filer the solution, allow the solution to stand still in a dryer, and evaporate the solvent to obtain a colorless transparent crystal with a yield rate of 87% and a purity of 99.2%.

Preferred Embodiment 4

Add 50 mg of a crude 4-hydroxy-2-oxo-1-pyrrolidineacetamide racemate in anhydrous methanol to obtain a saturated solution. Now, a larger amount of suspended substance occurs. Heat the solution at 38° C. and stir the solution for 10 hours. Filer the suspended precipitate, and dry the suspended precipitate in vacuum for 24 hours. The precipitate powder is the 4-hydroxy-2-oxo-1-pyrrolidineacetamide racemate crystal produced with a yield rate 80% and a purity 99.5%.

Preferred Embodiment 5

Add 50 mg of a crude 4-hydroxy-2-oxo-1-pyrrolidineacetamide racemate in anhydrous methanol to obtain a saturated solution. Now, a larger amount of suspended substance occurs. Heat the solution at 40° C. and stir the solution overnight. Filer the suspended precipitate, and dry the suspended precipitate in vacuum for 24 hours. The precipitate powder is the 4-hydroxy-2-oxo-1-pyrrolidineacetamide racemate crystal produced with a yield rate 80% and a purity 99.3%.

Preferred Embodiment 6

Add 50 mg of a crude 4-hydroxy-2-oxo-1-pyrrolidineacetamide racemate in isopropanol to obtain a saturated solution. Now, a larger amount of suspended substance occurs.

Heat the solution at 40° C. and stir the solution for 7 hours. Filer the suspended precipitate, and dry the suspended precipitate in vacuum for 24 hours. The precipitate powder is the 4-hydroxy-2-oxo-1-pyrrolidineacetamide racemate crystal produced with a yield rate 88% and a purity 99.5%.

Preferred Embodiment 7

Add 50 mg of a crude 4-hydroxy-2-oxo-1-pyrrolidineacetamide racemate in isopropanol to obtain a saturated solution. Now, a larger amount of suspended substance occurs. Heat the solution at 42° C. and stir the solution for 12 hours. Filer the suspended precipitate, and dry the suspended precipitate in vacuum for 20 hours. The precipitate powder is the 4-hydroxy-2-oxo-1-pyrrolidineacetamide racemate crystal produced with a yield rate 80% and a purity 99.3%.

Preferred Embodiment 8

Add 50 mg of a crude 4-hydroxy-2-oxo-1-pyrrolidineacetamide racemate in isopropanol to obtain a saturated solution. Now, a larger amount of suspended substance occurs. Heat the solution at 43° C. and stir the solution for 11 hours. Filer the suspended precipitate, and dry the suspended precipitate in vacuum for 18 hours. The precipitate powder is the 4-hydroxy-2-oxo-1-pyrrolidineacetamide racemate crystal produced with a yield rate 90% and a purity 99.2%.

Preferred Embodiment 9

Add 50 mg of a crude 4-hydroxy-2-oxo-1-pyrrolidineacetamide racemate in butanol to obtain a saturated solution. Now, a larger amount of suspended substance occurs. Heat the solution at 45° C. and stir the solution for 6 hours. Filer the suspended precipitate, and dry the suspended precipitate in vacuum for 20 hours. The precipitate powder is the 4-hydroxy-2-oxo-1-pyrrolidineacetamide racemate crystal produced with a yield rate 80% and a purity 99.4%.

Preferred Embodiment 10

The 4-hydroxy-2-oxo-1-pyrrolidineacetamide racemate crystal form I is tested as follows.

A Bruker D8 Advanced Diffractometer is used to obtain a powder diffraction chart of the crystalline 4-hydroxy-2-oxo-1-pyrrolidineacetamide racemate obtained in Preferred Embodiment 1, and the testing conditions are listed below: Cu Kα, 40 kV, 40 mV is the light source, the step length is 0.12°, the scanning speed is 10°/min, the scanning range is 5~45°, and room temperature. In the X-ray diffraction chart, the crystalline 4-hydroxy-2-oxo-1-pyrrolidineacetamide racemate crystal form has a diffraction peak at a diffraction angle 2θ including 12.011, 15.318, 17.407, 19.633, 21.228, 22.052, 24.577, 25.223, 27.647, 28.161, 29.109, 30.805, 31.276, 31.766, 32.77, 33.477, 35.252, 35.645, 36.236, 37.379, 39.56, 40.489, 41.256, 41.948, 43.443 and 44.628.

The powder X-ray diffraction chart of the crystalline 4-hydroxy-2-oxo-1-pyrrolidineacetamide racemate of the present invention is expressed by a lattice spacing d, a Bragg angle (2θ) and a relative intensity percentage I as follows:

| 2θ/degree | d/Å | Relative Intensity I/% |
|---|---|---|
| 12.011 | 7.3623 | 3.6 |
| 15.318 | 5.7794 | 11.6 |
| 17.407 | 5.0905 | 34.7 |
| 19.633 | 4.5179 | 51.2 |
| 21.228 | 4.1820 | 100.0 |
| 22.052 | 4.0275 | 5.8 |
| 24.577 | 3.6192 | 49.1 |
| 25.223 | 3.5278 | 6.4 |
| 27.647 | 3.2238 | 15.6 |
| 28.161 | 3.1661 | 13.2 |
| 29.109 | 3.0652 | 10.4 |
| 30.805 | 2.9002 | 1.3 |
| 31.276 | 2.8576 | 1.4 |
| 31.766 | 2.8146 | 5.6 |
| 32.770 | 2.7306 | 12.3 |
| 33.477 | 2.6746 | 5.6 |
| 35.252 | 2.5438 | 5.0 |
| 35.645 | 2.5167 | 8.4 |
| 36.236 | 2.4770 | 7.9 |
| 37.379 | 2.4038 | 1.9 |
| 39.560 | 2.2762 | 2.3 |
| 40.489 | 2.2261 | 3.7 |
| 41.256 | 2.1865 | 1.5 |
| 41.948 | 2.1520 | 2.6 |
| 43.443 | 2.0813 | 1.8 |
| 44.628 | 2.0287 | 1.3 |

FIG. 1 shows the X-diffraction powder chart of the crystalline 4-hydroxy-2-oxo-1-pyrrolidineacetamide racemate of the invention, and this chart is consistent to the data of the power chart of a single crystalline 4-hydroxy-2-oxo-1-pyrrolidineacetamide racemate reported by CCDC.

Figure 2:
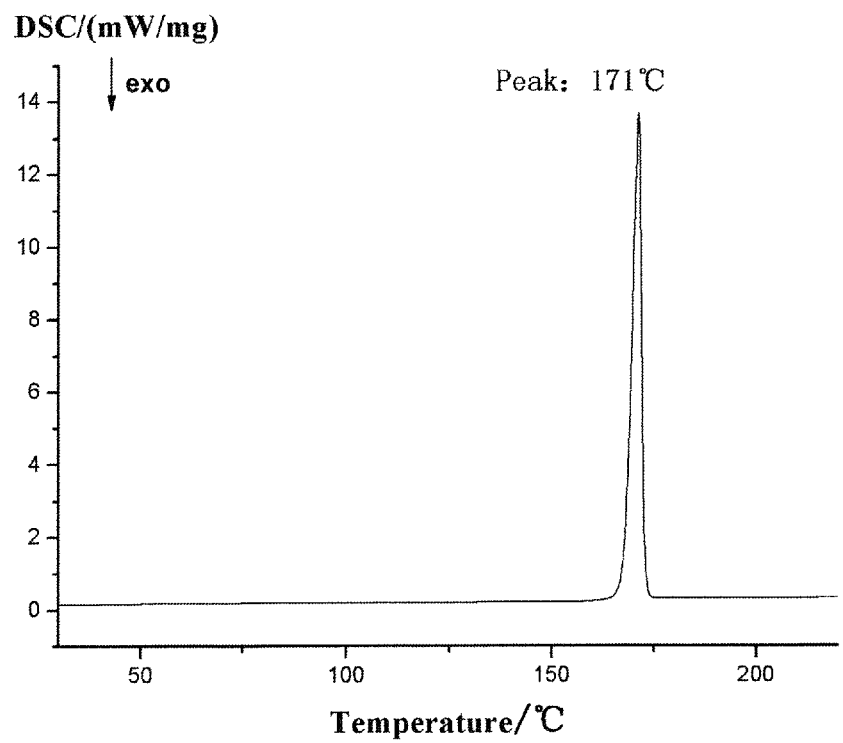
FIG. 2 is a differential scanning calorimetry chart (DSC) of a 4-hydroxy-2-oxo-1-pyrrolidineacetamide racemate crystal form I of the present invention.

FIG. 2 shows the differential scanning calorimetry chart (DSC) of the crystalline 4-hydroxy-2-oxo-1-pyrrolidineacetamide racemate of the invention, and the endothermic transition temperature is 171° C.

Figure 3:
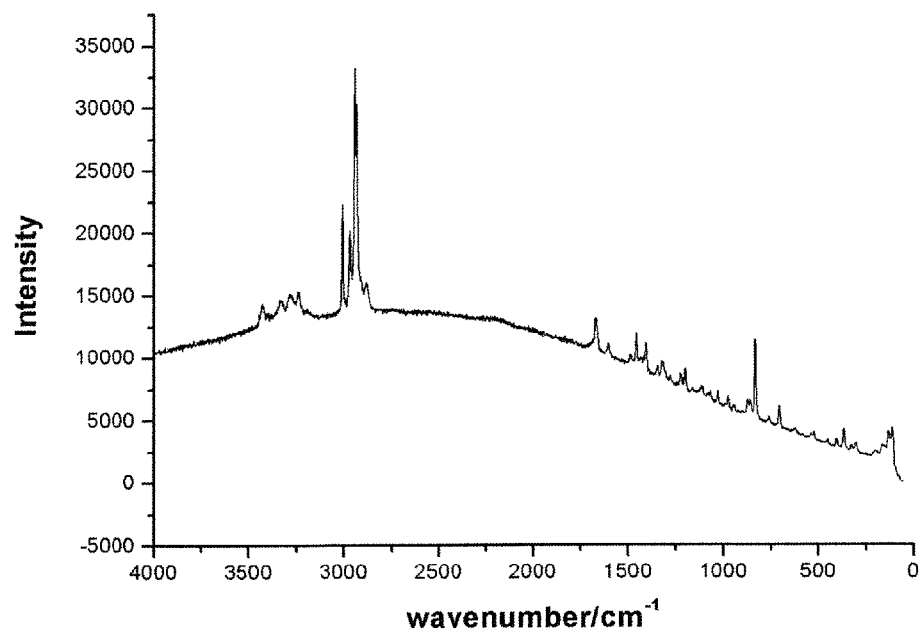
FIG. 3 is a Raman spectrogram of a 4-hydroxy-2-oxo-1-pyrrolidineacetamide racemate crystal form I of the present invention.

FIG. 3 shows the Raman spectrograph of the crystalline 4-hydroxy-2-oxo-1-pyrrolidineacetamide racemate of the invention.

Figure 5:
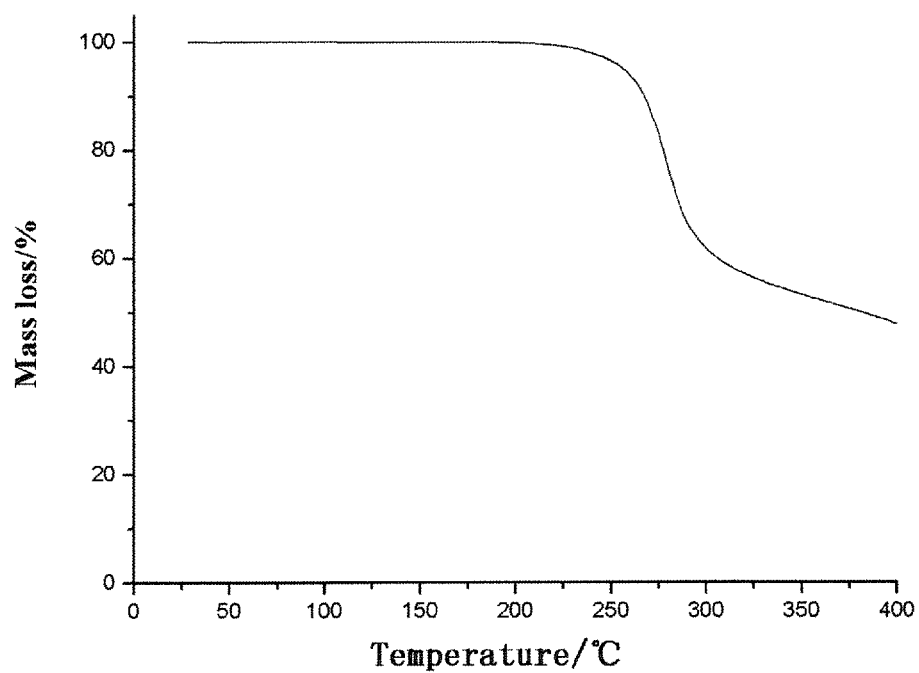
FIG. 5 is a thermal gravimetric analysis (TGA) chart of a 4-hydroxy-2-oxo-1-pyrrolidineacetamide racemate crystal form I of the present invention.

FIG. 5 shows the thermal gravimetric analysis (TGA) chart of the crystalline 4-hydroxy-2-oxo-1-pyrrolidineacetamide racemate of the invention.

Figure 4:
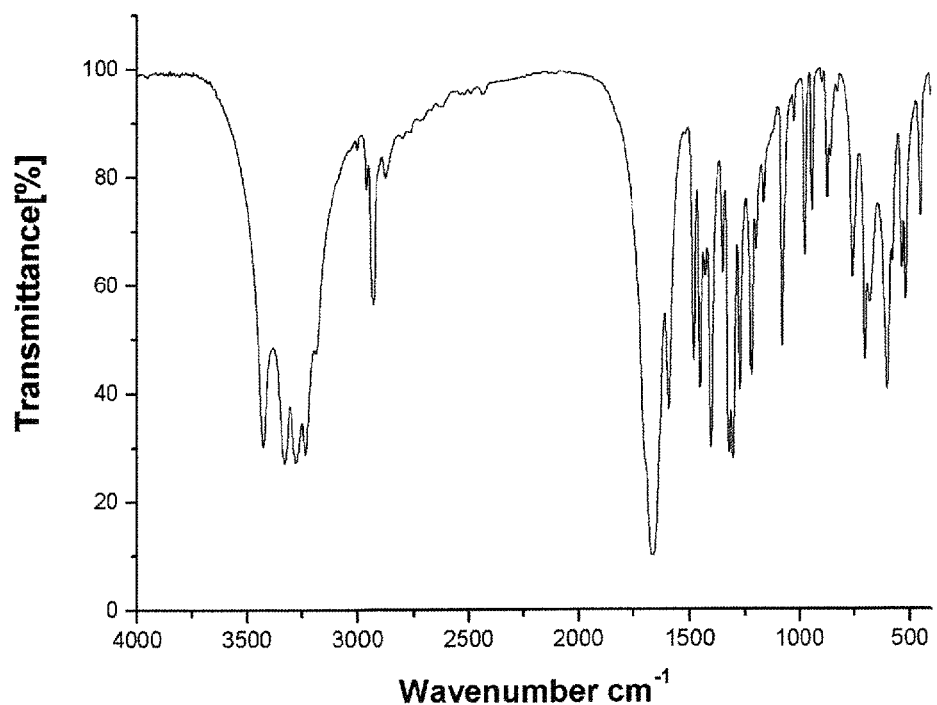
FIG. 4 is an infrared (IR) spectrogram of a 4-hydroxy-2-oxo-1-pyrrolidineacetamide racemate crystal form I of the present invention.

FIG. 4 shows the infrared spectrograph of the crystalline 4-hydroxy-2-oxo-1-pyrrolidineacetamide racemate of the invention, and an absorption peak occurs at a wave number such as 3426, 3330, 3276, 3235, 2931, 2876, 1665, 1593, 1480, 1452, 1428, 1320, 1272, 1220, 1078, 974, 941, 757, 702, 602, 517, or 450 cm$^{-1}$.

While the invention has been described by means of specific embodiments, numerous modifications and variations could be made thereto by those skilled in the art without departing from the scope and spirit of the invention set forth in the claims.

What is claimed is:

1. A 4-hydroxy-2-oxo-1-pyrrolidineacetamide racemate crystal form I, having a diffraction peak at a diffraction angle 2θ selected from the group consisting of 12.011, 15.318, 17.407, 19.633, 21.228, 22.052, 24.577, 25.223, 27.647, 28.161, 29.109, 30.805, 31.276, 31.766, 32.77, 33.477, 35.252, 35.645, 36.236, 37.379, 39.56, 40.489, 41.256, 41.948, 43.443 and 44.628 degrees.

2. The 4-hydroxy-2-oxo-1-pyrrolidineacetamide racemate crystal form I according to claim 1, having X-ray diffraction powder data expressed by the following d (Å) values and relative intensity percentage I values (%),

| d value | I value | d value | I value |
| --- | --- | --- | --- |
| 7.3623 | 3.6 | 5.7794 | 11.6 |
| 5.0905 | 34.7 | 4.5179 | 51.2 |
| 4.1820 | 100.0 | 4.0275 | 5.8 |
| 3.6192 | 49.1 | 3.5278 | 6.4 |
| 3.2238 | 15.6 | 3.1661 | 13.2 |
| 3.0652 | 10.4 | 2.9002 | 1.3 |
| 2.8576 | 1.4 | 2.8146 | 5.6 |
| 2.7306 | 12.3 | 2.6746 | 5.6 |
| 2.5438 | 5.0 | 2.5167 | 8.4 |
| 2.4770 | 7.9 | 2.4038 | 1.9 |
| 2.2762 | 2.3 | 2.2261 | 3.7 |
| 2.1865 | 1.5 | 2.1520 | 2.6 |
| 2.0813 | 1.8 | 2.0287 | 1.3. |

3. The 4-hydroxy-2-oxo-1-pyrrolidineacetamide racemate crystal form I according to claim 1 having a X-ray diffraction powder chart as shown in FIG. 1.

4. The 4-hydroxy-2-oxo-1-pyrrolidineacetamide racemate crystal form I according to any one of claims 1 to 3, having an absorption peak in an infrared spectrum produced by the 4-hydroxy-2-oxo-1-pyrrolidineacetamide racemate crystal form I in a wave number selected from the group consisting of: 3426 ($cm^{-1}$), 3330 ($cm^{-1}$), 3276 ($cm^{-1}$), 3235 ($cm^{-1}$), 2931 ($cm^{-1}$), 2876 ($cm^{-1}$), 1665 ($cm^{-1}$), 1593 ($cm^{-1}$), 1480 ($cm^{-1}$), 1452 ($cm^{-1}$), 1428 ($cm^{-1}$), 1320 ($cm^{-1}$), 1272 ($cm^{-1}$), 1220 ($cm^{-1}$), 1078 ($cm^{-1}$), 974 ($cm^{-1}$), 941 ($cm^{-1}$), 757 ($cm^{-1}$), 702 ($cm^{-1}$), 602 ($cm^{-1}$), 517 ($cm^{-1}$), and 450 ($cm^{-1}$).

5. A method of preparing the 4-hydroxy-2-oxo-1-pyrrolidineacetamide racemate crystal form I of any one of claims 1 to 3, comprising the steps of:
   (1) dissolving a crude 4-hydroxy-2-oxo-1-pyrrolidineacetamide racemate in a micromolecular alcohol to obtain a saturated solution;
   (2) heating and stirring the saturated solution overnight at 38-42° C. to obtain a suspended precipitate;
   (3) filtering and drying the suspended precipitate to obtain a crystal.

6. The method for preparing the 4-hydroxy-2-oxo-1-pyrrolidineacetamide racemate crystal form I of claim 5, wherein the micromolecular alcohol is isopropanol; and the stirring temperature is approximately 40° C., and the stirring time is approximately 7 hours.

7. The method for preparing the 4-hydroxy-2-oxo-1-pyrrolidineacetamide racemate crystal form I of claim 5, comprising the steps of:
   (1) dissolving a crude 4-hydroxy-2-oxo-1-pyrrolidineacetamide racemate in isopropanol to obtain a saturated solution and precipitating a suspended substance;
   (2) heating and stirring the solution containing the suspended substance to obtain a saturated solution, and stirring the saturated solution for 7 hours to obtain a suspended precipitate;
   (3) filtering and drying the suspended precipitate in vacuum for 24 hours to obtain a powdered crystal.

8. The method for preparing the 4-hydroxy-2-oxo-1-pyrrolidineacetamide racemate crystal form I of claim 6, wherein the micromolecular alcohol is isopropanol; and the stirring temperature is approximately 40° C., and the stirring time is approximately 7 hours.

9. The method for preparing the 4-hydroxy-2-oxo-1-pyrrolidineacetamide racemate crystal form I of claim 6, comprising the steps of:
   (1) dissolving a crude 4-hydroxy-2-oxo-1-pyrrolidineacetamide racemate in isopropanol to obtain a saturated solution and precipitating a suspended substance;
   (2) heating and stirring the solution containing the suspended substance to obtain a saturated solution, and stirring the saturated solution for 7 hours to obtain a suspended precipitate;
   (3) filtering and drying the suspended precipitate in vacuum for 24 hours to obtain a powdered crystal.

10. A method of preparing the 4-hydroxy-2-oxo-1-pyrrolidineacetamide racemate crystal form I of claim 4, comprising the steps of:
   (1) dissolving a crude 4-hydroxy-2-oxo-1-pyrrolidineacetamide racemate in a micromolecular alcohol to obtain a saturated solution;
   (2) heating and stirring the saturated solution overnight at 38-42° C. to obtain a suspended precipitate;
   (3) filtering and drying the suspended precipitate to obtain a crystal.

* * * * *